United States Patent [19]

Baumann et al.

[11] Patent Number: 5,220,048

[45] Date of Patent: Jun. 15, 1993

[54] SUBSTITUTED BENZOCYCLOBUTENES, A PROCESS FOR THEIR PREPARATION AND THEIR USE

[75] Inventors: Marcus Baumann, Basel; Walter Fischer; Vratislav Kvita, both of Reinach; Carl W. Mayer, Reihen, all of Switzerland

[73] Assignee: Ciba-Geigy Corporation, Ardsley, N.Y.

[21] Appl. No.: 356,826

[22] Filed: May 24, 1989

[30] Foreign Application Priority Data

May 27, 1988 [CH] Switzerland .......................... 2008/88
Jul. 19, 1988 [CH] Switzerland .......................... 2755/88

[51] Int. Cl.$^5$ .......................... C07F 7/08; C07F 7/18; C07F 7/10
[52] U.S. Cl. .......................... 556/489; 556/419; 556/415; 556/422; 556/438; 556/431; 558/387; 558/388; 558/406; 558/410; 558/411; 568/583; 568/626; 568/634; 568/56; 560/8; 560/10; 560/17; 560/21; 560/43; 562/427; 562/435; 562/457; 564/161; 564/191

[58] Field of Search ................ 568/634, 583, 626, 56; 556/431, 415, 419, 422, 438, 489; 558/387, 388, 406, 410, 411; 560/8, 10, 17, 21, 43; 562/427, 435, 457; 564/161, 191

[56] References Cited

U.S. PATENT DOCUMENTS 4,666,925 5/1987 Sun .................................. 568/634 X
4,935,560 6/1990 Klaus et al. .................... 568/634 X

OTHER PUBLICATIONS

"Chem. Abs. ", vol. 112, No. 234999r, 1990.
Cava et al., JACS vol. 72 pp. 17105-1705 (1957).
Barton et al., J. Chem Soc. Perkins Trans. vol. 1, pp. 967-971.
McOmie et al., Synthesis, vol. 7, pp. 416-417 (1973).

*Primary Examiner*—Paul F. Shaver
*Attorney, Agent, or Firm*—Kevin T. Mansfield

[57] ABSTRACT

Benzocyclobutene-1,2-dichlorides, -bromides and -iodides which are substituted in the benzene ring are accessible in good yields and short reaction times by reacting substituted 1,2-(dichloromethyl or dibromomethyl)-benzenes with NaI in acetonitrile as the solvent. They can be used together with dienophils, for example 1,4-quinones, in Diels-Alder reactions.

16 Claims, No Drawings

SUBSTITUTED BENZOCYCLOBUTENES, A PROCESS FOR THEIR PREPARATION AND THEIR USE

The invention relates to benzocyclobutene-1,2-dichlorides, -dibromides and -diiodides which are substituted in the benzene ring; to their preparation by reacting corresponding 1,2-bis-(dichloromethyl or dibromomethyl)-benzenes with NaI, and to their use together with dienophils in Diels-Alder reactions.

M. P. Cava et al describe, in J. Am. Chem. Soc. 72, pages 1701-1705 (1957), the preparation of benzocyclobutenes which are brominated and/or iodinated in the 1,2-position by reacting 1,2-bis-(dibromomethyl)-benzene with NaI in ethanol as solvent. The same method is used by J. W. Barton et al, J. Chem. Soc. Perkin Trans. 1, pages 967-971 (1986) for the preparation of 1,2,4,5-tetrabromobenocyclobutene. Admittedly relatively good yields are achieved; the long reaction time of 48 hours is, however, disadvantageous. J. W. McOmie et al report, in Synthesis 7, pages 416-417 (1973), that the corresponding ortho-quinodi-(bromomethane) is formed, as a reactive intermediary product, from 1,2-bis-(dibromomethyl)-4,5-dimethoxybenzene with NaI in dimethylformamide as solvent, and reacts with dienophils to give Diels-Alder adducts. 1,2-Dihalogenobenzocyclobutenes which are substituted in the benzene ring otherwise than with bromine or chlorine are not known. It has been found that these surprisingly stable compounds are obtained in good yields and short reaction times if the reaction of 1,2-bis-(dihalogenomethyl)-benzenes substituted in the benzene ring with NaI is carried out in the presence of acetonitrile.

The invention relates to compounds of the formula I

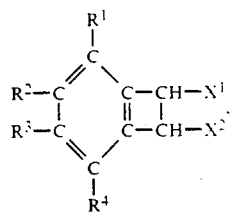

in which $X^1$ and $X^2$ independently of one another are —Cl, —Br or —I, and $R^1$, $R^2$, $R^3$ and $R^4$ independently of one another are —F, —CF$_3$, —CN, —NO$_2$, C$_1$-C$_{18}$alkoxy, C$_1$-C$_{18}$alkylthio, C$_6$-C$_{18}$aryl, C$_6$-C$_{16}$aryloxy or C$_6$-C$_{16}$arylthio, trialkylsilyl having 3 to 18 C atoms, —COOR$^5$ in which R$^5$ is H, or a radical of a C$_1$-C$_{18}$ alcohol diminished by a hydroxyl group, or —COX in which X is —NH$_2$ or the monovalent radical of a primary or secondary amine having 1 to 18 C atoms, and 1 to 3 of the groups R$^1$ to R$^4$ independently of one another are H, —Cl or —Br and the fourth of the groups R$^1$ to R$^4$ defined above.

$X^1$ and $X^2$ are preferably either —Br or —I, and it is preferable for R$^1$, or R$^1$ and R$^4$, or R$^1$, R$^2$ and R$^4$ to be a hydrogen atom.

As alkoxy and alkylthio, R$^1$-R$^4$ can be linear or branched and preferably contain 1 to 12, particularly 1 to 6 and especially 1 to 4, C atoms. Examples are alkoxy and alkylthio radicals of methyl, ethyl and the isomers of propyl, butyl, pentyl, hexyl, heptyl, octyl, nonyl, decyl, undecyl, dodecyl, tridecyl, tetradecyl, pentadecyl, heptadecyl and octadecyl.

If R$^1$-R$^4$ are aryl or a radical containing aryl, examples of the aryl group are naphthyl or particularly phenyl. In a preferred subgroup, R$^1$-R$^4$ as aryl or a radical containing aryl are phenyl, phenoxy or phenylthio.

As trialkylsilyl, R$^1$-R$^4$ preferably contain 3 to 14, particularly 3 to 8, C atoms. Examples of alkyl groups have been mentioned above. Some examples are trimethylsilyl, triethylsilyl, dimethylethylsilyl, tributylsilyl and dimethylbutylsilyl.

As the radical of an alcohol, R$^5$ preferably contains 1-12, particularly 1 to 6, C atoms. R$^5$ can, for example, be linear or branched alkyl, C$_5$cycloalkyl or C$_6$cycloalkyl which is unsubstituted or substituted by C$_1$-C$_6$alkyl, or C$_6$-C$_{13}$aryl which is unsubstituted or substituted by C$_1$-C$_6$alkyl or C$_6$-C$_{12}$aryl-C$_x$H$_{2x}$ in which x is 1 to 4. Aryl is preferably phenyl and x is preferably 1. R$^5$ is preferably H, C$_1$-C$_{18}$alkyl, especially C$_1$-C$_{12}$alkyl and particularly C$_1$-C$_6$alkyl, cyclohexyl, cyclopentyl, phenyl or benzyl. Some examples are methyl, ethyl, the isomers of propyl, butyl, pentyl, hexyl, heptyl, octyl, nonyl, decyl, undecyl, dodecyl, tetradecyl, hexadecyl and octadecyl, cyclopentyl, cyclohexyl, methylcyclohexyl, phenyl, benzyl, methylphenyl, dimethylphenyl, ethylphenyl, methylethylphenyl, t-butylphenyl and methylbenzyl. It is particularly preferable for R$^5$ to be methyl or ethyl.

As primary or secondary amino, X preferably contains 1 to 18, particularly 1 to 12 and especially 1 to 8, C atoms. X can have the formula —NR$^6$R$^7$ in which R$^6$ and R$^7$ independently of one another are H, linear or branched C$_1$-C$_{18}$alkyl, particularly C$_1$-C$_{12}$alkyl and especially C$_1$-C$_6$alkyl, cyclopentyl, cyclohexyl, phenyl or benzyl, or R$^6$ and R$^7$ together are tetramethylene or pentamethylene or 3-oxa-1,5-pentylene. Some examples are dimethylamino, diethylamino, ethylmethylamino, dibutylamino, dioctylamino, methyldodecylamino, didodecylamino, methyloctadecylamino, phenylmethylamino, benzylmethylamino, pyrrolino, piperidino and morpholino.

In a preferred group of compounds of the formula I, one or two of the groups R$^1$ to R$^4$ are —Cl or —Br. In another preferred group, R$^2$ is —Cl or —Br, R$^1$ and R$^4$ are H and R$^3$ is as defined above. A preferred embodiment of compounds of the formula I is constituted by those in which R$^1$, R$^2$, R$^3$ and R$^4$ are —F, —CF$_3$, —CN, —NO$_2$, C$_1$-C$_{12}$alkoxy, C$_1$-C$_{12}$alkylthio, Si(CH$_3$)$_3$, COOR$^5$ in which R$^5$ is C$_1$-C$_{18}$alkyl, or —COX in which X is —NR$^6$R$^7$ in which R$^6$ and R$^7$ independently of one another are H, C$_1$-C$_{18}$alkyl, cyclohexyl, cyclopentyl, phenyl or benzyl, or R$^6$ and R$^7$ together are tetramethylene or pentamethylene or 3-oxa-1,5-pentylene, and 1 to 3 of the groups R$^1$, R$^2$, R$^3$ and R$^4$ independently of one another are H, —Cl or —Br and the fourth of the groups R$^1$, R$^2$, R$^3$ and R$^4$ is as defined above. A subgroup of the preferred embodiment is constituted by compounds of the formula I in which R$^2$, R$^3$ and R$^4$ are —F, —CF$_3$, —CN, —NO$_2$, C$_1$-C$_6$alkoxy, C$_1$-C$_6$alkylthio, —Si(CH$_3$)$_3$, —COOC$_1$-C$_{12}$alkyl or —CONR$^6$R$^7$ in which R$^6$ and R$^7$ independently of one another are H or C$_1$-C$_{12}$alkyl, and R$^1$ or R$^1$ and R$^4$ is/are H.

The invention also relates to a process for the preparation of compounds of the formula I, which comprises reacting a compound of the formula II

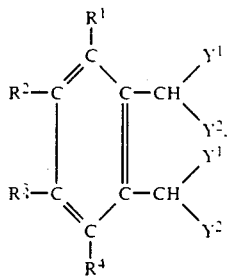

(II)

in which $R^1$, $R^2$, $R^3$ and $R^4$ are as defined above and $Y^1$ and $Y^2$ independently of one another are —Cl or —Br, with NaI in the presence of acetonitrile or acetone at a temperature of at least 40° C.

$Y^1$ and $Y^2$ are preferably either —Cl or —Br. The reaction is advantageously carried out under conditions of reflux. It is advantageous to use the acetonitrile as the solvent. The NaI is generally added in excess. It is preferable to use at least one mole up to a ten fold molar excess of NaI, relative to the compounds of the formula II.

The isolation of the compounds of the formula I can be effected in a manner generally known, for example removing the acetonitrile in vacuo, taking up the residue in an organic solvent, washing the solution with a reducing agent to remove iodine formed, drying and removing the solvent. The residue can be purified in a customary manner by distillation, crystallization or chromatographic methods.

A replacement of —Cl or —Br by —I can take place in the course of the reaction, so that compounds of the formula I in which $X^1$ and $X^2$ are —Cl or —Br can contain compounds of this type in which $X^1$ is —Cl or —Br and $X^2$ is —I or $X^1$ and $X^2$ are I. These mixtures are embraced by the invention.

The compounds of the formula II are known in part or can be prepared by known and analogous processes, for example by chlorinating or brominating correspondingly substituted o-xylenes or phthalaldehydes. Substituted o-xylenes and phthalaldehydes are obtainable by generally known methods.

The compounds of the formula I are valuable diene components which, together with dienophils, form Diels-Alder adducts in high yields. The invention also relates to the use of compounds of the formula I as a diene component together with a dienophil, particularly unsubstituted or substituted benzo-1,4-quinones or naphtho-1,4-quinones, maleic anhydride or maleimide, in Diels-Alder reactions. Substituted anthra-1,4-quinones, naphtacene-5,12-quinones or naphthaline-2,3-dicarboxylic anhydrides or naphthaline-2,3-dicarboximides are obtained in these reactions. Anthraquinones and naphthacenequinones can, for example, be used as photosensitizers (cf. U.S. Pat. No. 3,941,759) or as photoinitiators, particularly naphthacene-5,12-quinones which are substituted at least in the 2-position by $C_1$-$C_{18}$ alkylthio or phenylthio. Anthraquinones can also be used in electrochromic displays (Japanese Preliminary Published Specification 61-43,680).

The compounds of the formula I and quinones which can be prepared from them are valuable intermediates for the preparation of substituted tetrathiotetracenes or tetraselenotetracenes (cf. U.S. Pat. No. 3,617,151). Electrically conductive charge-transfer complexes (CT complexes) can be prepared from such chalkogenated tetracenes by means of electron acceptors. It is possible to attach them to polymers by means of their functional groups, for example to incorporate them into polymers as side groups (cf. U.S. Pat. No. 4,617,151). The CT complexes are also suitable for the production, for example, of antistatic coatings of photographic film elements, magnetic tapes, electrophotographic film elements and electronic components (see U.S. Pat. No. 3,634,336). The chalkogenated tetracenes also exhibit electrochromic properties; they can be used for electrochromic displays. They are also suitable for use as laser-optical data storage units [Nach. Chem. Techn. Lab. 35, pages 255 et seq. (1987)] and as anode material in organic solid state batteries (EP-A 0,090,598). CT complexes of substituted tetrathiotetracenes or tetraselenotetracenes can also be incorporated into thermoplastic, thermosetting or elastomeric polymers in order to achieve antistatic properties. For this purpose it is advantageous to dissolve, for example, substituted or unsubstituted tetrathiotetracenes or tetraselenotetracenes together with a soluble polymer or a precursor thereof and an electron acceptor, for example an agent which forms halogen (organic halogenated compounds, for example bromoform, trichlorobromomethane, tetrabromomethane, hexachloropropane, perchlorobutadiene, 1,3-dichloro-2-butene, 1,4-dichloro-2-butene, 1,4-bis(trichloromethyl)benzene, iodoacetonitrile, iodoform, tetrachloroethylene, perchlorocyclobutadiene, N-chlorosuccinimide, N-bromosuccinimide or N-iodosuccinimide), if appropriate together with a further inert solvent, and to remove by evaporation at an elevated temperature the excess agent which forms halogen and the solvent. The resulting composition contains in the polymer a network of needle-shaped crystals of the CT complex, if the chalkogenated tetracene is unsubstituted or contains small substituents (for example F, $CH_3$ or $CF_3$). Compositions of this type exhibit a high electrical conductivity. This can be improved further, if a substituted tetrathiotetracene or tetraselenotetracene which has been prepared from the compounds of the formula I and which does not form a network of this type and is present in a state of fine distribution in the polymer matrix is concomitantly used, since substituted tetrathiotetracenes or tetraselenotetracenes of this type have no tendency, or only a slight tendency, to crystallize in the polymer.

The following examples illustrate the invention in greater detail.

A) PREPARATION EXAMPLES

Examples 1–7

A mixture of 0.03 mol of appropriately substituted 1,2-bis-(dibromomethyl)-benzene, 0.18 mol of sodium iodide and 100 ml of acetonitrile is heated under reflux for 1–2 hours with stirring. After cooling, the mixture is extracted several times with hexane and the hexane phase is washed with $NaHSO_3$ solution. After the removal of the hexane by evaporation, the residue is purified by distillation or crystallization and/or chromatography. The mixtures of substituted 1,2-dibromobenzocyclobutenes or 1,2-bromoiodobenzocyclobutenes shown in Table 1 are obtained in this manner.

TABLE 1

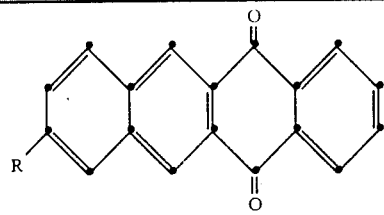

(A)                (B)

| Example | R² | R³ | Yield % | Boiling point Melting point | Compound A(%) | Compound B(%) | Mass spectrum M_A⁺/% | Mass spectrum M_B⁺/% | Notes |
|---|---|---|---|---|---|---|---|---|---|
| 1 | H | OCH₃ | 43 | 150° C. 0.013 mbar | 5 | 95 | 292/0.3 | 338/1 | a) |
| 2 | H | NO₂ | 19 | 112–113° C. | 5 | 95 | 307/0.1 | 353/4 | b) |
| 3 | H | COOCH₃ | 63 | — | 55 | 45 | 320/42 | 366/0.1 | c) |
| 4 | H | F | 42 | 100° C. 0.052 mbar | 55 | 45 | 280/4 | 326/2 | d) |
| 5 | H | Me₃Si | 80 | — | 58 | 42 | 334/42 | — | c) |
| 6 | Me₃Si | Me₃Si | 7 | — | 66 | 33 | 406/23 | 570/6 | e) |
| 7 | COOCH₃ | COOCH₃ | 41 | 69–71° C. | 53 | 47 | 378/60 | — | f) |
| 8 | CF₃ | H | 63 | — | 55 | 45 | 330/10 | 377/4 | c) |
| 9 | CF₃ | CF₃ | 45 | — | 56 | 44 | 398/35 | 444/8 | c) | a) After cooling, the reaction mixture is evaporated to dryness, the residue is partitioned between ether and water, and the ether phase is washed with NaHSO₃ solution. After the removal of the ether by evaporation the residue is distilled in a high vacuum.
b) The procedure is the same as that under a). The residue is chromatographed over silica gel (hexane – 0.5% of ethyl acetate) and then crystallized from cyclohexane.
c) The procedure is the same as that under a). The residue is chromatographed over silica gel (hexane – 0.5% of ethyl acetate).
d) Purification by distillation
e) The residue is chromatographed in hexane over silica gel
f) The residue is chromatographed using CH₂Cl₂ over silica and is recrystallized from methanol.

B) USE EXAMPLES

Examples 10–11

A mixture of 1 mol of substituted 1,2-dibromobenzocyclobutene and 1,2-bromoiodobenzocyclobutene, 1.5 mol of naphthoquinone and 7 l of dichlorobenzene is heated under reflux. After cooling, the precipitated anthracene-5,12-quinone is filtered off and is purified by crystallization or sublimation in a high vacuum. Further details are to be found in Table 2.

Example 12

Production of an electrically conductive polymer film

Reacting naphtho-1,4-quinone with the compound from Example 4 gives 9-fluoronaphthacene-5,12-quinone which is converted into 2-fluoro-5,6,11,12-tetraselenotetracene by the process described in U.S. Pat. No. 4,522,754, Examples c) to e).

100 mg of polyether-sulfone [(OC₆H₄—C(CH₃)₂—C₆H₄—O—C₆H₄—SO₂O—C₆H₄)ₙ] and 1.6 mg of 2-fluoro-5,6,11,12-tetraselenotetracene are dissolved in 6.0 g of dimethylformamide. This solution is mixed with a solution of 4.2 mg of hexachloropropane in 2 ml of dimethylformamide. The solution is poured onto a heated sheet of glass, and the solvent is evaporated at 120° C. The volume resistivity of the polymer film formed is 0.56 ohm×cm.

What is claimed is:

1. A compound of formula I (I)

[structure of anthracene-5,12-quinone with R substituent]

| Example | R | Reaction time (hr) | Purification | Yield (%) | Melting point (°C.) | Mass spectrum (M⁺/%) |
|---|---|---|---|---|---|---|
| 10 | —COOCH₃ | 16 | Recrystallization from toluene | 10 | 268 | 316/100 |
| 11 | —NO₂ | 4 | Sublimation at 200° C. | 22 | >270 | 303/100 |

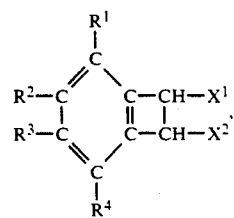

in which

X¹ and X² are independently —Cl, —Br or —I, $R^1$ and $R^4$ are hydrogen.

$R^2$ and $R^3$ are independently —F, —CF$_3$, —CN, —NO$_2$, C$_1$-C$_{18}$-alkoxy, C$_1$-C$_{18}$-alkylthio, C$_6$-C$_{18}$-aryl, C$_6$-C$_{16}$-aryloxy or C$_6$-C$_{16}$-arylthio, trialkylsilyl having 3 to 18 C atoms, —COOR$^5$ in which R$^5$ is hydrogen or a radical of a C$_1$-C$_{18}$-alcohol diminished by a hydroxyl group; or —COX in which X is —NH$_2$ or a monovalent radical of a primary or secondary amine having 1 to 18 carbon atoms; or where one of R$^2$ and R$^3$ is H, —Cl or —Br and the other of R$^2$ and R$^3$ is as defined above.

2. A compound according to claim 1, in which X$^1$ and X$^2$ are —Br or —I.

3. A compound according to claim 1 wherein R$^2$ and R$^3$ are —F, —CF$_3$, —CN, —NO$_2$, C$_1$-C$_{12}$-alkoxy, C$_1$-C$_{12}$-alkylthio, —Si(CH$_3$)$_3$, —COOR$^5$ in which R$^5$ is C$_1$-C$_{18}$-alkyl; or —COX in which X is —NR$^6$R$^7$ in which R$^6$ and R$^7$ are independently H, C$_1$-C$_{18}$-alkyl, cyclohexyl, cyclopentyl, phenyl or benzyl, or R$^6$ and R$^7$ together are tetramethylene, pentamethylene or 3-oxa-1,5-pentylene, or where one of R$^2$ and R$^3$ is H, —Cl or —Br, and the other of R$^2$ and R$^3$ is as defined above.

4. A compound according to claim 1, in which R$^2$ is H.

5. A compound according to claim 1, in which R$^2$, R$^3$ and as alkoxy and alkylthio, contain 1 to 12 C atoms.

6. A compound according to claim 1, in which R$^2$, R$^3$ and as aryl or as a radical containing aryl, are phenyl, phenoxy or phenylthio.

7. A compound according to claim 1, in which R$^2$, R$^3$ and as trialkylsilyl, contain 3 to 14 C atoms.

8. A compound according to claim 1, in which R$^5$ is H, C$_1$-C$_{18}$alkyl, cyclohexyl, cyclopentyl, phenyl or benzyl.

9. A compound according to claim 1, in which X has the formula —NR$^6$R$^7$ in which R$^6$ and R$^7$ independently of one another are H, C$_1$-C$_{18}$alkyl, cyclohexyl, cyclopentyl, phenyl or benzyl, or R$^6$ and R together are tetramethylene, pentamethylene or 3-oxa-1,5-pentylene.

10. A compound according to claim 1, in which R$^2$ is —Cl or —Br, R$^1$ and R$^4$ are H and R$^3$ is as defined in claim 1.

11. A compound according to claim 3, in which R$^2$ and R$^3$ and R$^4$ are —F, —CF$_3$, —CN, —NO$_2$, C$_1$-C$_6$alkoxy, C$_1$-C$_6$alkylthio, —Si(CH$_3$)$_3$, —COOC$_1$-C$_{12}$alkyl or —CONR$^6$R$^7$ in which R$^6$ and R$^7$ independently of one another are H or C$_1$-C$_{12}$alkyl.

12. An improved process for the preparation of a compound of formula I

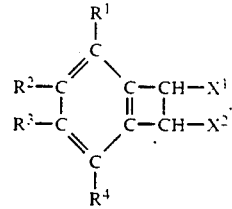

in which
X$^1$ and X$^2$ are independently —Cl, —Br or —I,
R$^1$ and R$^4$ are hydrogen,
R$^2$ and R$^3$ are independently —F, —CF$_3$, —CN, —NO$_2$, C$_1$-C$_{18}$-alkoxy, C$_1$-C$_{18}$-alkylthio, C$_6$-C$_{18}$-aryl, C$_6$-C$_{16}$-aryloxy or C$_6$-C$_{16}$-arylthio, trialkylsilyl having 3 to 18 C atoms, —COOR$^5$ in which R$^5$ is hydrogen or a radical of a C$_1$-C$_{18}$-alcohol diminished by a hydroxyl group; or —COX in which X is -NH$_2$ or a monovalent radical of a primary or secondary amine having 1 to 18 carbon atoms; or where one of R$^2$ and R$^3$ is H, —Cl or —Br and the other of R$^2$ and R$^3$ is as defined above, wherein a compound of formula II

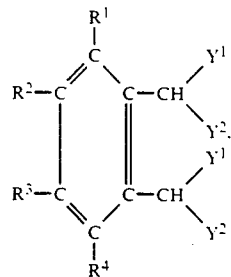

where Y$^1$ and Y$^2$ are independently —Cl or —Br, is reacted with sodium iodide in the presence of a solvent at reflux conditions at a temperature of at least 40° C., wherein the improvement comprises carrying out the reaction in acetonitrile or acetone as the solvent.

13. A process according to claim 12, wherein Y$^1$ and Y$^2$ in formula I are either —Cl or —Br.

14. A process according to claim 12, wherein at least 1 mole up to a ten fold molar excess of NaI is used, relative to the compound of the formula II.

15. A process according to claim 12, wherein acetonitrile is the solvent.

16. The compound according to claim 1 which is a mixture of 1,2-dibromo-4-methoxybenzocyclobutene, 1-bromo-2-iodo-4-methoxybenzocyclobutene, and 1-iodo-2-bromo-4-methoxybenzocyclobutene.

* * * * *